United States Patent [19]

Kaiser et al.

[11] Patent Number: 4,780,405
[45] Date of Patent: Oct. 25, 1988

[54] CARBONIC ANHYDRASE INHIBITOR-TAGGED NUCLEIC ACID PROBES

[75] Inventors: Emil T. Kaiser, New York, N.Y.; Gary F. Musso; Soumitra Ghosh, both of San Diego, Calif.; Orgel Leslie E., La Jolla, Calif.; Geoffrey M. Wahl, San Diego, Calif.

[73] Assignee: Siska Diagnostics, Inc., LaJolla, Calif.

[21] Appl. No.: 753,176

[22] Filed: Jul. 9, 1985

Related U.S. Application Data

[63] Continuation-in-part of Ser. No. 748,499, Jun. 25, 1985, abandoned.

[51] Int. Cl.$^4$ .............................................. C12Q 1/68
[52] U.S. Cl. .......................................... 435/6; 435/7; 536/26; 536/27; 536/28; 935/78; 935/77; 436/501; 548/136; 548/303; 549/223
[58] Field of Search ................... 435/6, 7; 536/27, 28, 536/26; 935/78, 77; 436/501; 548/136, 303; 549/223

[56] References Cited

U.S. PATENT DOCUMENTS 4,134,792  1/1979  Boguslaski et al. ................. 436/815

FOREIGN PATENT DOCUMENTS 0063879  3/1982  European Pat. Off. .
0097373  1/1984  European Pat. Off. .
8403285  8/1984  European Pat. Off. .

OTHER PUBLICATIONS

Draper et al. "A Method for Linking Fluorescent Labels to Polynucleotides Application to Studies of Ribosome-Ribonucleic Acid Interactions," Biochemistry, 1980,19,1774–1781.
Draper, "Attachment of Reporter Groups to Specific Selected Cytidine Residues in RNA using a Bisulfite-Catalyzed Transamination Reaction," Nucleic Acids Research, 1987, 12, 989–1002.
Mumford et al. "Purification of a membrane-bound metalls-endopeptidase from porcine kidney that degrades peptide hormones," PNAS, 78, Nall pp. 6623–6627, Nov. 1981.
Nitta et al., "A New Reaction Useful for Chemical Cross-Linking Between Nucleic Acids and Proteins," FEBS Letters 166, 194–198 (1984).
Negishi et al., "N$^4$-Aminocytidine: Formation, Reactivity, and Mutagenicity," Nucl. Acids Res., Symp. Ser. No. 12, 29–30 (1983).
Negishi et al. "N$^4$-Aminocytidine, A nucleoside Analog that Has an Exceptionally High Mutagenic Activity," Nucl. Acids Res. 11, 5223–5233 (1983).
Smith, "Hydrazine Derivatives," *The Chemistry of Open-Chain Organic Nitrogen Compounds*, vol. II, pp. 119–209. W. A. Benjamin, N.Y., N.Y. (1966).
Leary, "A Staining Procedure for Cattle and Bison Carbonic Anhydrase Using Fluorescein Diacetate," Anim. Blood. Grps. Biochem. Genet. 9, 65–67 (1978).
Epton et al., "Water-Soluble Coloured Covalent Conjugates of Carbonic Anhydrase and N-(sym-Trinitroaryl)polyacrylamide/Acrylhydrazide Co-Polymers," Biochem. Soc. Trans. 5, 277–279 )1977).
Livesey, "On the Colorimetric Method of Assaying Carbonic Anhydrase (EC 4.2.1.1)," Anal. Biochem. 77, 552–561 (1977).
Whitney et al., "Inhibition of Human Erythrocyte Carbonic Anhydrase B by Chloroacetyl Sulfonamides with Labeling of the Active Site," J. Biol. Chem. 242, 4206–4211 (1967).
Langer et al., "Enzymatic Synthesis of Biotin-labeled Polynucleotides Novel Nucleic Acid Affinity Probes," Proc. Natl. Acad. Sci. (U.S.A.) 78, 6633–6637 (1981).
Chu and Orgel, "Detection of Specific DNA Sequences with Short Biotin-labeled Proves," DNA 4, 327–331 (1985).
Chu and Orgel, "Nonenzymatic Sequence-specific Cleavage of Single-stranded DNA," Proc. Natl. Acad. Sci. (U.S.A.) 82, 963–976 (1985).
Chu et al., "Derivatization of Unprotected Polynucleotides," Nucl. Acids Res. 11, 6513–6529 (1983).
Hayatsu, "Bisulfite Modification of Nucleic Acids and their Constitutents," Pro. in Nucl. Acid Res. and Mol. Biol. 16, 75–124 (1976).

Primary Examiner—Robert J. Warden
Assistant Examiner—Carol A. Spiegel
Attorney, Agent, or Firm—Fitch, Even, Tabin & Flannery

[57] ABSTRACT

Nucleic acid hybridization probes are provided which comprise nucleoside bases or terminal nucleotide phosphates chemically linked to aromatic sulfonamide inhibitors of carbonic anhydrase. Methods of preparing probes of the invention, intermediates used in such methods, and methods of using the probes of the invention in hybridization assays are also provided. A probe of the invention is detected by binding to it a reporter group, such as a homopolymer or heteropolymer of enzymes, which includes a carbonic anhydrase which binds to the inhibitor linked to the probe, and then detecting the bound reporter group, as by production of a fluorescent or colored product in a reaction catalyzed by an enzyme component of the reporter group. Also provided are enzyme immunoassays wherein detection of antibody is by a process which comprises a chemical reaction catalyzed by a carbonic anhydrase.

20 Claims, No Drawings

CARBONIC ANHYDRASE INHIBITOR-TAGGED NUCLEIC ACID PROBES

RELATED APPLICATION

This application is a continuation-in-part of copending application Ser. No. 748,499, filed June 25, 1985, and entitled: "Nucleic Acid Probes Comprising $N^4$-(Substituted Amino)Cytidines"

TECHNICAL FIELD

The present invention relates to nucleic acid hybridization probes. More particularly, it relates to probes chemically labeled with inhibitors of a carbonic anhydrase enzyme and to processes for making such probes and using them in hybridization assays.

BACKGROUND OF THE INVENTION

The use of single-stranded DNA or RNA probes, to test for the presence of particular DNAs or RNAs and associated biological entities in samples of biological material, is well known. See, e.g., Grunstein and Hogness, Proc. Nat'l. Acad. Sci. (US) 72, 3961–3965 (1975); Southern, J. Mol. Biol. 98, 503–505 (1975); Langer et al., Proc. Nat'l. Acad. Sci. (US) 78, 6633–6637 (1981); Falkow and Moseley, U.S. Pat. No. 4,358,535; Ward, et al., European Patent Application Publication No. 0 063 879; Englehardt, et al., European Patent Application Publication No. 0 097 373; Meinkoth and Wahl, Anal. Biochem. 138, 267–284 (1984).

Among areas in which such probes find application are testing of food and blood for contamination by pathogenic bacteria and viruses; diagnosis of fungal, bacterial and viral diseases by analysis of feces, blood or other body fluids; diagnosis of genetic disorders, and certain diseases such as cancers associated with a genetic abnormality in a population of cells, by analysis of cells for the absence of a gene or the presence of a defective gene; and karyotyping. See Klausner and Wilson, Biotechnology 1, 471–478 (1983); Englehardt, et al. supra; Ward et al., supra; Falkow and Moseley, supra.

The principle which underlies the use of such probes is that a particular probe, under sufficiently stringent conditions, will, via hydrogen-bonding between complementary base moieties, selectively hybridize to (single-stranded) DNA or RNA which includes a sequence of nucleotides ("target sequence") that is complementary to a nucleotide sequence of the probe ("probing sequence" specific for the target sequence). Thus, if a biological entity (e.g., virus, microorganism, normal chromosome, mammalian chromosome bearing a defective gene) to be tested for has at least one DNA or RNA sequence uniquely associated with it in samples to be tested, the entity can be tested for using a nucleic acid probe.

A DNA or RNA associated with an entity to be tested for and including a target sequence to which a nucleic acid probe hybridizes selectively in a hybridization assay is called "target" DNA or RNA, respectively, of the probe.

A probe typically will have at least 8, and usually at least 12, ribonucleotides or 2'-deoxyribonucleotides in the probing sequence that is complementary to a target sequence in its target DNA or RNA. Outside the probing sequences through which a probe complexes with its target nucleic acid, the probe may have virtually any number and type of bases, as long as the sequences including these additional bases do not cause significant hybridization with nucleic acid other than target nucleic acid under hybridization assay conditions. That is, a probe will be specific for its target DNA or RNA in hybridization assays.

To be useful in analyzing biological samples for the presence of a target DNA or RNA, a polynucleotide probe must include a feature which will render detectable the duplex formed when the probe is hybridized to its complementary sequence in the target (single-stranded) DNA or RNA. Typically, such features in a probe include radioactive atoms or pyrimidine or purine bases chemically modified to include moieties which are readily and sensitively detected by any of a number of techniques.

For example, a probe may be made with $^{32}P$-labelled nucleoside triphosphates; then the probe itself, as well as target DNA or RNA with the probe hybridized to it, can be detected by means of radiation from $^{32}P$-decay.

Probes whose detectability is based on radioactive decay are unsuitable for many applications because of safety problems and licensing requirements associated with radioactive materials and because of degradation of the probes that occurs with radioactive decay during storage. Thus, probes whose detectability is based on chemical modification of pyrimidine or purine bases are preferred in many situations.

There are numerous examples of modified purine or pyrimidine bases in probes wherein a moiety, herein referred to as a "tag moiety," is chemically linked to render detectable target DNA or RNA hybridized with probe. See, e.g. Ward et al., supra; Englehardt et al., supra; Klausner and Wilson, supra. Typically, the "tag moiety" is a moiety to which a protein will bind with high affinity, e.g. an antigen to which an antibody binds; a biotinyl or iminobiotinyl moiety to which avidin or streptavidin will bind; an inhibitor of an enzyme to which the enzyme binds. A protein which binds with high affinity to a tag moiety of a probe is referred to herein as a "conjugate protein" of the tag moiety.

In a typical assay, after probe is hybridized to target DNA or RNA, a "reporter group" is added to the system and binds to the tag moiety or moieties of the hybridized probe. A "reporter group" provides a signal which renders detectable the probe that is hybridized to target DNA or RNA. A typical reporter group is a conjugate protein of the tag moiety or a complex, involving such a conjugate protein, which binds to tag through the binding site for tag in the conjugate protein. The reporter group so bound is then detected by an appropriate immunological, physical, or biochemical technique. For example, if the reporter group is simply a conjugate protein, detection might be by any of a number of well known immunoassay techniques, based on antibodies directed against the conjugate protein. If the reporter group is a conjugate protein which naturally contains a chromophore or fluorophore, or is a conjugate protein modified to include such a moiety, detection might be by a spectroscopic technique based on the chromophore or fluorophore. If the reporter group is a heteropolymer or homopolymer of enzymes, including a conjugate protein, detection could involve detection of substances produced by enzymatic reactions catalyzed by enzymes in the polymer. Ward et al., supra, Englehardt, et al., supra, and Klausner and Wilson, supra, describe a number of techniques for assaying reporter groups bound to tag moieties of probes.

A tag moiety itself, without being bound by a reporter group, might provide detectability to a probe. For example, a tag moiety which is a fluorophore or chromophore can be detected with a suitable spectroscopic technique without binding of a reporter group. See, e.g., Bauman et al., J. Histochem. Cytochem. 29, 227-237 (1981).

In some cases wherein pyrimidine or purine bases are chemically modified by the addition of a tag moiety, a linking moiety will separate the tag moiety from the site of modification on the pyrimidine or purine base. See, e.g., the Ward et al. and Englehardt et al. references, supra. In some cases, such linking moieties facilitate the attachment of tag moieties to probe. Further, a linking moiety tends to hold a tag moiety some distance from the modified purine or pyrimidine base, thereby increasing accessibility of the tag moiety to binding by a reporter group and, further, reducing interference with formation or stability of duplexes between probe and target DNA or RNA in those instances where the tag moiety has a large molecular weight.

Polynucleotide probes which comprise at least one cytosine moiety modified to have a tag moiety linked, directly or through a linking moiety, to the $N^4$-position, have not been available heretofore.

Further, prior to the present invention, it was not realized that inhibitors of a carbonic anhydrase enzyme can be employed as tag moieties for polynucleotide probes and that a probe so tagged can be detected through binding to the tag moiety a reporter group which includes a carbonic anhydrase as conjugate protein.

Because the amino group at the 4-position of cytosine is involved in hydrogen-bonding between cytosine and guanine moieties in nucleic acid duplexes, it has been thought heretofore that modifications to this amino group would be unacceptable in nucleic acid probes. It has been thought that such modifications in a nucleic acid would interfere with duplex formation, and thereby result in a probe with unacceptable specificity and sensitivity, by severely disrupting guanosine-cytosine hydrogen-bonding. See Ward et al., supra; Ruth, Patent Cooperation Treaty International Publication No. WO84/032185 (1984).

The chemistry of modifying cytosine moieties at the $N^4$-nitrogen has been studied with cytidine and 2'-deoxycytidine and their phosphates, both as monomers and included in single-stranded polynucleotides. Nitta et al., FEBS Letters 166, 194-198 (1984); Negishi et al. (I), Nucl. Acids Res. Symp. Series 12, pp. 29-30 (1983); Negishi et al., (II), Nucl. Acids Res. 11, 5223-5333 (1983); Hayatsu, Prog. Nucleic Acid Res. and Mol. Biol. 16, 75-124 (1976).

The $N^4$-amino group, in $N^4$-aminocytidine and $N^4$-amino-2'-deoxycytidine and their phosphates, both as monomers and included in single-stranded polynucleotides, is known to have reactivities characteristic of substituted hydrazines and reacts accordingly with aldehydes, ketones, isothiocyanates and imidates. Nitta et al., supra; Negishi (I), supra; Hayatsu, supra. See also P. Smith, The Chemistry of Open-Chain Organic Nitrogen Compounds, W. A. Benjamin, Inc., New York, N.Y., Vol. II, pp. 119-209 (1966).

Nitta et al., supra, have reported transamination of cytosine moieties in polycytidine with hydrazine in the presence of bisulfite; and derivatization of the transaminated product with an adduct of glutathione with pyruvic acid, wherein the adduct reacts through the keto-carbon of pyruvate with the $N^4$-amino group.

Whitney et al., J. Biol. Chem. 242, 4206-4211 (1967) describe aromatic sulfonamide inhibitors of mammalian erythrocyte carbonic anhydrase B. Epton, at Biochem. Soc. Trans. 5, 277-279 (1977), has described preparation of enzymatically active polymers of mammalian erythrocyte carbonic anhydrase B. Assays for detecting carbonic anhydrase activity are described by Leary, Anim. Blood Grps. Biochem. Genet. 9, 65-67 (1978) and Livesey, Anal. Biochem. 77, 552-561 (1977).

SUMMARY OF THE INVENTION

We have discovered nucleic acid probes which include a tag moiety which is an aromatic sulfonamide inhibitor of a carbonic anhydrase.

We have discovered, further, novel compounds, which can be used to link carbonic anhydrase inhibitor tag moieties to nucleoside bases or terminal phosphates of polynucleotides to make polynucleotide probes of the invention, and novel methods to make probes of the invention which comprise reacting the novel compounds with suitably modified nucleoside bases or terminal phosphates of polynucleotides which have sequences of probes.

We have discovered, further, a method of detecting a nucleic acid probe of the invention, which method comprises binding to the aromatic sulfonamide tag moiety of the probe a reporter group which includes as conjugate protein a carbonic anhydrasse that is inhibited by the tag moiety.

Duplexes between the probes of the invention and target DNA and RNA to which they bind are also part of our discovery, as are the duplexes complexed with the conjugate reporter groups which include carbonic anhydrase as conjugate protein.

Our invention encompasses a novel method for testing a sample for the presence of a biological entity, associated with a target DNA or RNA. Such method comprises combining single-stranded DNA or RNA, derived from the sample, with a nucleic acid probe of the invention specific for the target DNA or RNA. Reaction conditions for carrying out the method are selected whereby stable duplexes form between probe and at least a portion of its target nucleic acid but significant duplex formation between probe and non-target nucleic acids present in the sample is excluded. The method also comprises detecting said stable duplexes by means of a signal from the carbonic anhydrase-containing reporter group, which is bound to the tag moiety of the probe.

Our invention further encompasses kits for carrying out the novel method of the invention for testing samples for the presence of a biological entity associated with a target DNA or RNA. In one embodiment, the kits comprise a probe according to the invention. In another embodiment, the kits comprise a probe according to the invention, a reporter group which includes a carbonic anhydrase as conjugate protein and which can be employed to detect the probe of the invention included in the kit, and reagents to generate a detectable signal with the reporter group included in the kit.

DETAILED DESCRIPTION OF THE INVENTION

In one aspect, the present invention is a nucleic acid probe which comprises (i) a nucleoside base modified to include a group ("modifying functional group") which comprises a tag moiety that is an aromatic sulfonamide inhibitor of a carbonic anhydrase or (ii) a terminal nucleotide bound through a terminal phosphate to a modifying functional group which comprises a tag moiety that is an aromatic sulfonamide inhibitor of a carbonic anhydrase.

Typically, a modifying functional group which comprises a tag moiety will also comprise a linking moiety.

By "terminal nucleotide" is meant the ribonucleotide or 2′-deoxyribonucleotide at either the 5′- or the 3′-end of a linear, nucleic acid single-strand. By "terminal phosphate" of a terminal nucleotide is meant a monophosphate group that is bonded to the 5′- or 3′-carbon of the ribose moiety of the terminal nucleotide but that is not part of the phosphodiester linkage to the ribose moiety of the nucleotide next to the terminal nucleotide.

In another aspect, the invention includes duplexes formed between a probe of the invention and its target DNA or RNA from a sample tested with the probe. The invention includes, further, such duplexes complexed with a reporter group conjugate to the tag moiety on the probe. Such reporter groups will include as conjugate protein a carbonic anhydrase that is inhibited by the tag moiety.

In yet another aspect, the invention relates to a method for testing a sample for a target DNA or RNA which comprises (i) combining, with the target DNA or RNA, a nucleic acid probe specific for the target DNA or RNA, said probe comprising (1) a nucleoside base modified to include a modifying functional group which comprises a tag moiety that is an aromatic sulfonamide inhibitor of a carbonic anhydrase or (2) a terminal nucleotide bound through a terminal phosphate to a modifying functional group that is an aromatic sulfonamide inhibitor of a carbonic anhydrase, provided that the derivation of single-stranded nucleic acid from said sample and the combining of said single-stranded nucleic acid with said probe are under conditions whereby stable duplexes form between the probe and at least a portion of the target nucleic acid but not significantly between the probe and non-target DNA or RNA; and (ii) determining whether stable duplex was formed in step (i) by (a) separating unduplexed probe from duplexed probe formed in step (i); (b) combining the duplexed probe with a reporter group which is conjugate to tag moiety of the probe and which includes as conjugate protein a carbonic anhydrase that is inhibited by said tag moiety, under conditions whereby the reporter group binds to at least a portion of any of said tag moiety that is present, and then separating from the product so treated substantially all reporter group not bound to said tag moiety; (c) treating the product of step (i), after treatment according to step (ii)(a) and step (ii)(b), to produce a signal from any of said bound reporter group that is present; and (d) determining whether a detectable signal is generated by the treatment of step (ii)(c). The treatment of step (ii)(c) will depend on the reporter group which is to provide the signal and on the type of signal to be provided. If, for example, the reporter group is a carbonic anhydrase conjugated to a fluorescent compound such as fluorescein or tetramethylrhodamine and the signal is to be fluorescence emission from the reporter group, the treatment can be simply exposure to electromagnetic radiation of wavelength suitable to stimulate the emission from the fluorescent moities of the reporter group. To cite another example, if the reporter group is a homopolymer of a carbonic anhydrase and the signal is to be the appearance of a visible color due to a reaction catalyzed by the enzyme, as in the fluorescein diacetate procedure described by Leary (1978), supra, the treatment will involve combination of the product of step (i), after treatment according to steps (ii)(a) and (ii)(b), with substrates for the enzyme and any other compounds necessary to produce the colored substance which is observed. The determination of step (ii)(d), of whether a detectable signal is generated, will involve observation, with the naked eye or with suitable instrumentation if necessary, to detect any signal that might be generated. Also, usually the method will be carried out in parallel on the sample being tested (test sample), a sample of nucleic acid known to be free of DNA or RNA with target segment of the probe (negative control), and possibly also a sample known to contain DNA or RNA with target segment of the probe (positive control). When the method is so carried out, in parallel on test sample, negative control and positive control, the determination will then involve comparing the signals from the samples to ascertain that the assay system was functional (producing a signal from the positive control that is greater than "background" signal, from the negative control) and whether the signal detected from the test sample was greater than "background" signal. When signal from test sample is determined to be greater than background signal, the test sample signal can be ascribed to target DNA or RNA in the test sample.

The invention entails also a number of kits for testing samples for the presence of a biological entity that is associated with a target DNA or RNA. One of said kits comprises (i) a quantity of a nucleic acid which has a sequence of a probe specific for said target DNA or RNA in samples to be tested and (ii) reagents to modify at least a portion of the bases or terminal nucleotides (through terminal phosphates) in said quantity of nucleic acid to have a group which comprises a tag moiety that is an aromatic sulfonamide inhibitor of a carbonic anhydrase. Another of said kits comprises a nucleic acid probe of the invention which has a sequence whereby the probe is specific for said target DNA or RNA in samples to be tested. Yet another of the kits according to the invention comprises a nucleic acid probe of the invention specific for said target DNA or RNA together with reporter group, which includes as conjugate protein a carbonic anhydrase which is inhibited by tag moiety on the probe. The preferred kits of the invention include, in addition to probe of the invention and reporter group conjugate to the probe, reagents necessary to generate a signal with the reporter group.

The invention entails further a compound of Formula XXXII $$R_{32}(CO)-R_{34}-R_{33} \quad \text{XXXII}$$

wherein $R_{32}$ is

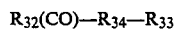

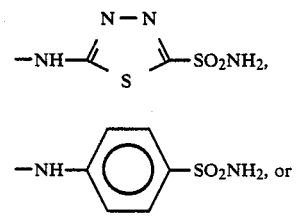

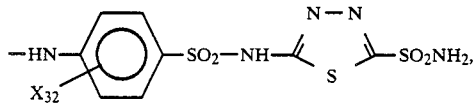

wherein $X_{32}$ is hydrogen, halogen or $-NO_2$; wherein $R_{34}$ is alkyl of 2 to 20 carbon atoms; and wherein $R_{33}$ is $-(C=O)R_2$, $CO_2H$, $-(CHR_2)OH$,

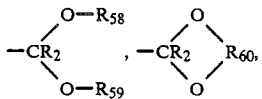

$-NH_2$, or $-N=C=R_3$, wherein $R_2$ is hydrogen or alkyl of 1 to 4 carbon atoms, $R_3$ is oxygen or sulfur, $R_{58}$ and $R_{59}$ are the same or different and are each alkyl of 1 to 5 carbon atoms, and $R_{60}$ is alkyl of 2 or 3 carbon atoms. "Halogen" means fluoro, chloro, bromo or iodo.

Compounds of Formula XXXII are intermediates in preparations of preferred probes of the invention.

The present invention also entails processes for making compounds of Formula XXXII. These processes are taught in examples below.

The invention entails further processes for making nucleic acid probes of the invention.

A process of the invention for making a nucleic acid probe of the invention, which comprises an $N_4$-(substituted amino)cytosine moiety for Formula LVII

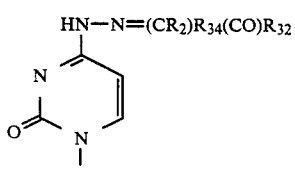   LVII wherein $R_2$, $R_{32}$ and $R_{34}$ are as defined above for Formula XXXII, comprises reacting a quantity of the nucleic acid with the same sequence as the probe and comprising an $N^4$-aminocytosine moiety of formula

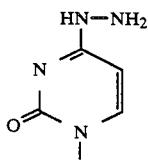

with a compound of Formula XXXIV

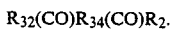   XXXIV

In the probes of the invention which comprise a moiety of Formula LVII and the process of the invention for making such probes by reacting nucleic acid comprising an $N^4$-aminocytosine with compound of Formula XXXIV, $R_2$, $R_{34}$, and $R_{32}$ in the moiety of Formula LVII and compound of Formula XXXIV are preferably as follows: $R_2$: hydrogen, $R_{34}$: n-alkyl of 2 to 20 carbon atoms (most preferably n-alkyl of 2 to 8 carbon atoms); and $R_{32}$:

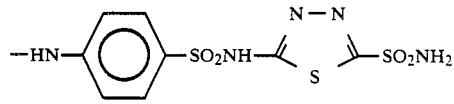

The amino group bonded to the $N^4$-nitrogen of cytosine in the $N^4$-aminocytosine moiety of formula

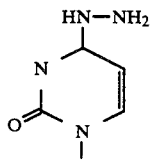

is referred to herein as the "$N^4$-amino group".

The moiety of formula

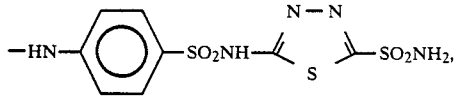

is referred to herein as PABSAT, for p-amino-benzenesulfonamide of aminothiadiazole.

Probes of the invention comprising a $N^4$-(substituted amino)cytosine moiety but with a hydrazine linkage in place of the hydrazone linkage indicated in Formula LVII can be prepared with probes with the hydrazone linkage by simply reducing the probe (with linked tag) after formation of probe with the hydrazone linkage.

Probes of the invention comprising an $N^4$-(substituted amino)cytosine moiety of Formula LVIII

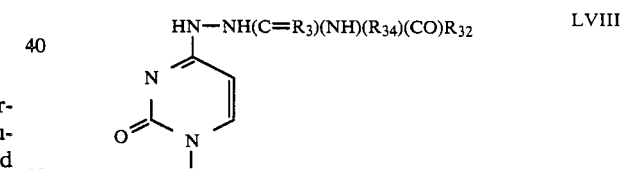   LVIII wherein $R_3$, $R_{32}$, and $R_{34}$ are as defined above for Formula XXXII are prepared by first preparing the compound of Formula XXXVI $R_{32}(CO)R_{34}(N=C=R_3)$   XXXVI by reaction of the compound of Formula XXXV $R_{32}(CO)R_{34}NH_2$   XXXV with phosgene (if $R_3$ is oxygen) or thiophosgene (if $R_3$ is sulfur) and then reacting the compound of Formula XXXVI with a nucleic acid with the same sequence as the probe and comprising a $N^4$-aminocytosine moiety. Preferably thiophosgene is employed in the process. Correspondingly, $R_3$ is preferably sulfur in the compounds of Formula XXXVI and the $N^4$-(substituted amino)cytosine moieties of Formula LVIII in probes of the invention.

The preferred probes of the invention are those wherein the tag is linked to the amino nitrogen of $N^4$-aminocytosines; among these, the more preferred are those with the hydrazone linkage, as indicated in Formula LVII.

A nucleic acid with the same sequence as a probe and comprising an $N^4$-aminocytosine can be provided by reacting a quantity of nucleic acid which has the same sequence as the probe with hydrazine in the presence of bisulfite to convert at least a portion of the cytosine moieties in said quantity of nucleic acid to $N^4$-aminocytosine moieties. This process is described in more detail in the Examples below.

A nucleic acid with the sequence of a probe can be made by any of various in vitro synthesis techniques known in the art followed by purification of the nucleic acid of desired sequence by high performance liquid chromatography (HPLC) or any other standard method known in the art. One of these techniques, involving automated solid-phase, step-wise chemical synthesis, utilizing phosphoramidite chemistry of Matteucci and Caruthers, and Beaucage and Caruthers, and purification of the nucleic acid of desired sequence by HPLC, is described in greater detail in Example I below.

When a nucleic acid with the sequence of the probe is prepared by an in vitro, step-wise chemical synthesis, the sequence of the entire nucleic acid will typically be complementary to the sequence of the particular segment of target DNA or RNA with which the probe is to hybridize in a hybridization assay. This segment of target DNA or RNA is referred to as the target segment corresponding to the probe.

A nucleic acid with the sequence of the probe can also be prepared in vivo. For example, a double-stranded nucleic acid which includes the sequence of the target segment can be isolated (as by restriction endonuclease cleavage from the chromosomal or episomal DNA of the biological entity to be tested for with the probe) or prepared chemically (as by step-wise solid phase synthesis of both strands followed by annealing of the strands after synthesis and purification) and then cloned using standard techniques in a standard cloning vector, such as pBR322. For example, the pBR322 with the target segment insert can be prepared in large quantities using standard preparative techniques for plasmid DNA, which may include growth of transformed E. coli in the presence of chloramphenicol for a number of doubling times to suppress chromosomal and enhance plasmid replication. The pBR322 with target segment insert can be isolated by known techniques. If target nucleic acid is double-stranded DNA or RNA, both strands of said pBR322 are useful as nucleic acid with sequence of probe. If target nucleic acid is single-stranded DNA or RNA, one or the other of the strands of the pBR322 will be nucleic acid with the sequence of the probe. The chemistry described in detail in the Examples, for transamination of cytosines and attachment of tag moieties to $N^4$-amino groups of the transaminated cytosines, can be carried out on the pBR322 in single-stranded form to prepare probe of the invention.

Another method for obtaining nucleic acid with the sequence of the probe is to insert a double-stranded segment which includes a target segment into RF-form DNA of a filamentous bacteriophage, such as M13mp8, M13mp9, M13mp18 or M13mp19, as are known in the art and commercially available, transforming a suitable strain of E. coli, such as E. coli JM101 or JM103, also known and commercially available, with the recombinant RF-form DNA, selecting and culturing the transformed E. coli by known techniques, isolating phage from the culture medium, and finally isolating the single-stranded phage DNA from the phage by standard techniques. When a segment is inserted into RF-DNA, half of the resulting phage population will have DNA which includes an insert with a sequence which is complementary to that of the insert in the other half. If target DNA or RNA is double-stranded, both types of phage DNA will be nucleic acid with sequence of probe. If target DNA or RNA is single-stranded, only half of the phage DNA will be nucleic acid with probe sequence. Of course, as the skilled will recognize, the DNA including the target segment can be inserted asymmetrically into RF-DNA so that all of the resulting phage population will have DNA with the same insert and all of the resulting phage DNA will be nucleic acid with sequence of probe. The phage DNA will be treated chemically as described in the Examples to transaminate cytosines and then link tags to $N^4$-amino groups of the transaminated cytosines to make a probe of the invention.

RNAs with sequences of probes can be prepared by in vitro chemical techniques, by employing suitably protected ribonucleosides in place of 2'-deoxyribonucleosides. RNAs with sequences of probes can also be prepared enzymatically by known techniques using suitable DNA templates.

Cytosines in RNAs can be transaminated and subsequently linked to tag using essentially the same chemistry as described in the Examples for DNAs.

Alternatively, rather than first preparing a nucleic acid with a sequence of the probe and then transaminating cytosines in the nucleic acid, the nucleic acid with the same sequence as the probe and comprising an $N^4$-aminocytosine can be made directly by in vitro synthesis, including enzymatic and solid-phase chemical, using suitable analogs of $N^4$-aminocytidine or $N^4$-amino-2'-deoxycytidine.

In still a further aspect, the invention provides processes for making nucleic acid precursors of probes according to the invention by step-wise, solid-phase syntheses using suitably protected analogs of $N^4$-aminocytidine or $N^4$-amino-2'-deoxycytidine. Example III teaches such a process utilizing the phosphoramidite chemistry of Matteucci and Caruthers, and Beaucage and Caruthers. In view of the teaching of Example III, similar processes involving other methods for step-wise chemical synthesis of polynucleotides, in solution or solid-phase, such as triester methods, will be apparent to the skilled.

The present invention entails novel, protected analogs of $N^4$- aminocytidine and $N^4$-amino-2'-deoxycytidine which are employed in the processes provided by the invention for in vitro, step-wise synthesis of nucleic acid precursors of probes according to the invention. Certain of these analogs are described in Example III; from those described, others will be apparent to the skilled in the art.

There are known in the art numerous nucleoside bases, other than $N^4$-aminoctyosine, that are modified to include a functional group that is suitable for linking to the base a tag moiety that is a sulfonamide inhibitor of a carbonic anhydrase. Such a modified nucleoside base can be included in a polynucleotide with the sequence of a probe, and a probe of the invention can then be made by reacting the polynucleotide with a compound which includes such a sulfonamide inhibitor tag moiety and which is suitable for linking the tag to the modified nucleoside base through the functional group of the modified base.

Preferred among these modified nucleoside bases are pyrimidines modified at the 5-position and purines modified at the 8-position.

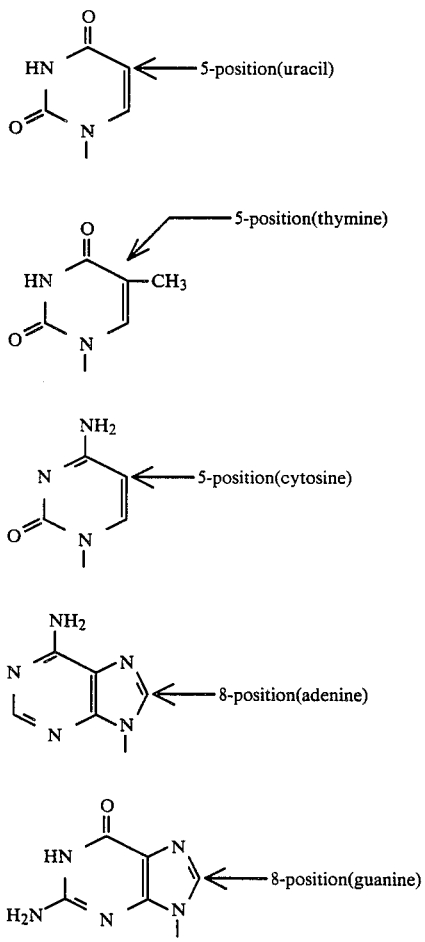

Ruth, in published patent cooperation treaty application No. WO 84/03285, teaches the step-wise, solid phase synthesis of polynucleotides which include, at selected positions in the sequence of the polynucleotide, a cytosine or uracil modified at the 5-position with a moiety of formula —$R_{50}R_{52}$ or an adenine or guanine modified at the 8-position with a moiety of formula —$Z_{50}R_{50}R_{52}$, wherein $Z_{50}$ is NH, S or O; $R_{50}$ is —CH$_2$—CHR$_{51}$—, —CH=CR$_{51}$—, —CHR$_{51}$—, —CH=CR$_{51}$(CO)NH— or —CH=CR$_{51}$(CO)—, wherein the —CH= or —CH$_2$— not bonded to R$_{51}$ is bonded to $Z_{50}$ or the carbon at the 5-position of uracil or cytosine, and wherein R$_{51}$ is hydrogen or alkyl of 1 to 6 carbon atoms; and wherein R$_{52}$ is —(CH$_2$)$_n$Y$_{52}$, wherein Y$_{52}$ is —NH$_2$, —CO$_2$H or an ester group, and n is 0 to 12. Step-wise solid phase synthesis is well suited for preparing nucleic acids of fewer than about 100 nucleotides with modified nucleoside bases at defined positions in the sequences.

Ward et al., supra, teach the synthesis of uridine and cytidine (as well as their nucleotides) modified at the 5-position of the base, and adenosine and guanosine (as well as their nucleotides) modified at the 8-position of the base, with —CH=CH—CH$_2$—NH$_2$ and —CH=CH—CH$_2$—O—CH$_2$CH(OH)CH$_2$NH$_2$.

Employing, along with unmodified nucleoside-5'-triphosphates, nucleoside-5'-triphosphates, wherein the nucleoside base is modified at the 5-position (if a pyrimidine) or the 8-position (if a purine), in a known nick-translation procedure as described in Ward et al., supra, and Langer et al., Proc. Nat'l. Acad. Sci. (U.S.A.) 78, 6633–6637(1981), utilizing as template a double-stranded DNA which includes a sequence complementary to that of a probe, a nucleic acid can be prepared which has the sequence of probe and comprises a nucleoside base modified at the 5-position (if pyrimidine) or 8-position (if purine) with a functional group which can be further reacted with a suitable compound, as described below, to yield a modifying functional group which comprises a tag moiety that is an aromatic sulfonamide inhibitor of a carbonic anhydrase. If a DNA-dependent RNA polymerase is employed in the "nick-translation" procedure in place of a DNA-dependent DNA polymerase, and ribonucleoside-5'-triphosphates are employed in place of 2'-deoxyribonucleoside-5'-triphosphates, an RNA can be prepared that, by reaction with a suitable compound, as described below, can be converted to an RNA probe of the invention. For these "nick-translation" procedures, particularly well suited modified nucleoside-5'-triphosphates are 2'-deoxyuridine-5'-triphosphate or, if RNA probe is to be prepared, uridine-5'-triphosphate wherein the uracil moiety has bonded to the carbon at the 5-position an allylamine moiety of formula —CH=CH—CH$_2$—NH$_2$.

A polynucleotide with the sequence of a probe and modified to comprise a pyrimidine modified at the 5-position or a purine modified at the 8-position with a functional group which has a terminal amino group (e.g., Y$_{52}$ is —NH$_2$) can be reacted, according to methods well known in the art, with a compound of Formula XL $$R_{32}(CO)-R_{34}-R_{40} \qquad XL$$

wherein R$_{40}$ is —CO$_2$H, —CHO, —N=C=S, —N=C=O, or an active ester group and R$_{32}$ and R$_{34}$ are as defined above for Formula XXXII, to prepare the probe of the invention. A compound of Formula XL wherein R$_{40}$ is an active ester group can be prepared by reacting, according to known procedures, the compound of Formula XL wherein R$_{40}$ is —CO$_2$H with a compound such as N-hydroxysuccinimide.

Similarly, a probe of the invention can be made by reacting, according to known methods, a compound of Formula XLI $$R_{32}(CO)R_{34}NH_2 \qquad XLI,$$

wherein R$_{32}$ and R$_{34}$ are as defined above for Formula XXXII with a polynucleotide with a sequence of a probe and modified to comprise a pyrimidine modified at the 5-position or a purine modified at the 8-position with a functional group which has a terminal —CO$_2$H or ester group (e.g., Y$_{52}$ is —CO$_2$H or an ester group).

After reaction of modified polynucleotide with compound for Formula XL or XLI, probe of the invention (wherein the group R$_{32}$ is linked to one or more bases of the polynucleotide) is isolated from unreacted reagents and purified by suitable chromotagraphic procedures, such as spin column chromotagraphy or high performance liquid chromatography, as known in the art.

Probes of the invention include polynucleotides which are modified, through a terminal phosphate of a terminal nucleotide of a polynucleotide with the sequence of a probe, with a modifying functional group which comprises a tag moiety that is an aromatic sulfonamide inhibitor of carbonic anhydrase. In such probes, none of the nucleoside bases of the polynucleotide needs to be modified. One means of preparing such a terminally tagged probe of the invention is to provide a polynucleotide with a sequence of probe and with a 5'-terminal phosphate group, react this polynucleotide with a carbodiimide, such as 0.1M 1-ethyl-3,3-dimethylaminopropyl carbodiimide, in the presence of imidazole-HCl buffer (e.g., 0.1M, pH 6) at room temperature for 4 to 8 hours, isolate the resulting 5'-phosphoimidazolide-derivatized polynucleotide chromatographically (e.g., by high performance liquid chromatography (HPLC)), and then react the 5'-phosphoimidazolide-derivatized polynucleotide with an excess of an amine-derivatized aromatic sulfonamide inhibitor of a carbonic anhydrase, such as a compound of Formula XLI, at a pH between about 7 to about 8 for 4 to 8 hours at room temperature. The resulting probe of the invention is isolated and purified by suitable chromatographic procedures, e.g., spin-column chromatography, HPLC, as known in the art. See Chu and Orgel, Proc. Nat'l Acad. Sci. (U.S.A.) 82, 963–967 (1985); Chu, Wahl and Orgel, Nucl. Acids Res. 11, 6513–6529 (1983).

Alternatively, probe of the invention can be prepared by direct condensation of polynucleotide with sequence of the probe and with a terminal 5'-phosphate by direct condensation of the polynucleotide with an amine-derivatized aromatic sulfonamide inhibitor of a carbonic anhydrase, such as a compound of Formula XLI, in the presence of methylimidazole-HCl buffer (e.g., 0.1M, pH 6) and 0.1M of a carbodiimide, such as 1-ethyl-3,3-dimethylaminopropyl carbodiimide, for 16–18 hours at room temperature followed by isolation of probe chromatographically. See Chu, Wahl and Orgel (1983), supra.

Probes of the invention are detected with a reporter group which includes carbonic anhydrase (carbonate hydrolyase, EC4.2.1.1) as conjugate protein. Preferred reporter group is polymerized carbonic anhydrase B from a mammalian (preferably bovine) erythrocyte, said polymer prepared as described bby Epton (1977), supra. A polymer of a mammalian erythrocyte carbonic anhydrase B prepared according to the procedure of Epton (1977), supra, is referred to in this specification as an "Epton polymer of carbonic anhydrase B". The preferred method of detecting bound carbonic anhydrase polymer is by the fluorescein diacetate assay of Leary (1978), supra. See also Livesey, Anal. Biochem. 77, 552–561 (1977). The fluorescein diacetate assay carried out essentially according to the procedure of Leary (1978) (See Example X, below) is referred to in the instant specification as the "fluorescein diacetate assay of Leary." Other detection systems (e.g., immunological, based on antibody-binding to carbonic anhydrase) may be employed.

Heteropolymers of carbonic anhydrase with other enzymes can be employed as reporter group. Such other enzymes include acid and alkaline phosphatase, beta-galactosidase, and horse radish peroxidase, for which detection systems are well known. See, e.g., Voller et al. "Enzyme-linked Immunosorbent Assay," in Manual of Clinical Immunology, N. Rose and H. Friedman, eds., American Society for Microbiology, Washington, D.C., 2nd Ed. (1980). These can be prepared, for example, by cross-linking the carbonic anhydrase with the other enzyme of the heteropolymer using standard techniques with bifunctional cross-linking reagents such as gluteraldehyde.

Carbonic anhydrase monomer or polymer can be derivatized with a chromophore or fluorophore and, bound to probe, detected spectrocopically by well known methods. Examples of fluorophore-labeled carbonic anhydrase reporter group are the monomer, or polymer prepared according to Epton, labeled by reaction, according to well known procedures, with isothiocyanate-derivatized or isocyanate-derivatized fluorescein, tetramethylrhodamine or tetraethylrhodamine.

Of course, apart from use as reporter groups with nucleic acid probes, carbonic anhydrase monomers and polymers can also be employed as the enzyme-component in enzyme immunoassay systems. For example, *Staphylococcus aureus* Protein A or an anti-IgG or anti-IgM can be labeled with carbonic anhydrase following procedures known in the enzyme-linked immunosorbent assay art for labeling Protein A or anti-immunoglobulins with acid or alkaline phosphatase, beta-galactosidase, or horseradish peroxidase. Attachment can be by cross-linking the proteins with any of various well known bifunctional cross-linking reagents such as glutaraldehyde. Alternatively, covalent attachment of an aromatic sulfonamide inhibitor of carbonic anhydrase to the Protein A or anti-immunoglobulin can first be carried out and then the inhibitor-derivatized Protein A or anti-immunoglobulin (before or after combining with antibody to be detected) can be combined with polymer of a carbonic anhydrase that is inhibited by the inhibitor. Protein A or anti-immunoglobulin labeled with carbonic anhydrase monomer or polymer can then be detected by the fluorescein diacetate assay of Leary (1978), supra, or any of the other of the above-described methods for detecting carbonic anhydrase monomer, homopolymer, or heteropolymer.

Covalent attachment of an aromatic sulfonamide inhibitor of a carbonic anhydrase to Protein A or an anti-immunoglobulin can, for example, be carried out by reacting, following known procedures, a compound of formula $R_{32}(CO)R_{34}R_{90}$, wherein $R_{32}$ and $R_{34}$ are as defined for Formula XXXII and $R_{90}$ is $-N{=}C{=}S$, $-N{=}C{=}O$, $-CHO$ or an active ester group. If $R_{90}$ is $-CHO$, the reaction with compound for formula $R_{32}(CO)R_{34}R_{90}$ is followed by reduction, as with $NaBH_4$. The derivatized protein is isolated by standard procedures, e.g., chromatographically.

It has not, heretofore, been recognized that carbonic anhydrase monomers and polymers can be employed as the enzyme component of enzyme immunoassays (i.e. immunoassays, such as enzyme-linked immunosorbent assays ("ELISAs") wherein detectability of presence of antibody in an assay system is provided by a reaction catalyzed by an enzyme). Thus, our invention includes enzyme immunoassays ("EIAs") wherein the enzyme, which provides detectability of antibody being assayed for, is a carbonic anhydrase. Perferably mammalian erythrocyte carbonic anhydrase B is employed in these immunoassays of our invention.

A nucleic acid probe of this invention comprises a nucleic acid of between about 12 to about 10,000 bases in length which comprises a terminal nucleotide bound through a terminal phosphate to a modifying functional group or (i) a cytosine or uracil modified by covalent attachment to position 5 of a group $-R_1$, (ii) an adenine or guanine modified by covalent attachment to position 8 of a group —$R_1$, or (iii) a cytosine modified by covalent attachment to the $N^4$nitrogen of a group —N=C($R_2$)—$R_8$, —NH—$CR_2HR_8$ or —NH(C=$R_3$)NH—$R_8$, wherein —$R_1$ is —$CH_2CHR_5R_6$, —$CH_2R_5R_6$, —CH=$CR_5R_6$, —CH=$CR_5$(CO)$R_6$ or —CH=$CR_5$(NH$R_6$), wherein $R_5$ is hydrogen or alkyl of 1 to 6 carbon atoms and $R_6$ is —(CH$_2$)$_m$$R_7$, wherein m is 0 to 12 and $R_7$ is —(-CO)(NH)$R_8$ or —(NH)(CO)$R_8$, wherein $R_8$ is —(CH$_2$)$_p$$R_{32}$, wherein p is 2 to 20 and $R_{32}$ is:

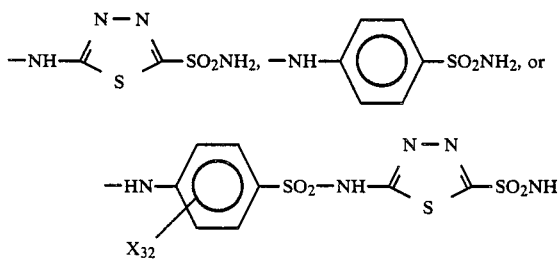

wherein $X_{32}$ is hydrogen, a halogen or —$NO_2$, wherein $R_2$ is hydrogen or alkyl of 1 to 4 carbon atoms, wherein $R_3$ is oxygen or sulfur. Preferred embodiments comprise probes wherein m is 0 to 6, more preferably m is 1 to 4; wherein p is 2 to 8; wherein the base length is between about 12 to about 100 bases; and wherein $R_{32}$ is 2-(p-amino-benzenesulfonamide)-1,3,4-aminothiadiazole.

A process for making a nucleic acid probe according to this invention comprises (i) a cytosine or uracil modified by covalent attachment to position 5 of a group —$R_1$ or (ii) an adenine or guanine modified by covalent attachment to position 8 of a group-$R_1$, wherein —$R_1$ is —$CH_2CHR_5R_6$, —CH=$CR_5R_6$, —$CHR_5R_6$, —CH=$CR_5$(CO)$R_6$ or —CH=$CR_5$(NH$R_6$), wherein $R_5$ is hydrogen or alkyl of 1 to 6 carbon atoms and $R_6$ is —(CH$_2$)$_m$$R_7$, wherein m is 0 to 12 and $R_7$ is —(-CO)(NH)$R_8$ or —(NH)(CO)$R_8$, wherein $R_8$ is —(CH$_2$)$_p$$R_{32}$, wherein p is 2 to 20 and $R_{32}$ is:

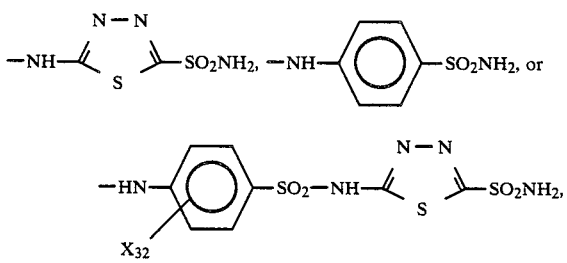

wherein $X_{32}$ is hydrogen, a halogen or —$NO_2$; and preferably wherein $R_1$ is —CH=$CR_5R_6$; wherein $R_5$ is hydrogen; wherein $R_6$ is —(CH$_2$)$_m$$R_7$; wherein m is 1 to 4; wherein $R_7$ is —(NH)(CO)$R_8$; wherein p is 2 to 8; and wherein $R_{32}$ is 2-(p-amino-benzenesulfonamide)-1,3,4-aninothiadiazole.

A probe of the invention is used in a hybridization assay for its target DNA or RNA (and, thereby, the biological entity associated with said target) using standard, known nucleic acid probe hybridization assay procedures. See Meinkoth and Wahl, supra, and references cited therein.

The assay of a sample will generally be carried out in parallel with an assay of a blank which contains approximately the same amount of nucleic acid as the sample but is known to contain no DNA or RNA with target segment for the probe (negative control) and may also be carried out in parallel with an assay of a sample known to contain target DNA or RNA (positive control).

The assay of test sample (or blank or positive control) typically proceeds as follows:

Typically, the assay will be carried out on a solid support, such as nitrocellulose paper, to which single-stranded nucleic acid binds non-covalently.

Nucleic acid of sample is isolated and affixed to the solid support in single-stranded form. These isolation and fixation procedures are carried out so that substantially all of the target segment corresponding to probe in any target nucleic acid present in the sample remains intact.

The solid support then may be prehybridized to substantially eliminate sites available on the support for the non-specific binding of probe.

Then a solution containing probe, in a 10-fold to $10^{12}$-fold, typically about $10^3$- to $10^6$-fold molar excess relative to target segment, is incubated with the solid support under conditions of stringency and for a time sufficient for stable duplex to form between probe and a substantial fraction (preferably nearly all) of any of its target segment on the filter but not to any significant extent between probe and segments other than target segments.

Then unduplexed or partly duplexed probe is washed from the system by a series of washes (usually 2 or 3) under stringency conditions and over usually short periods of time (minutes) to ensure that substantially only probe stably duplexed to target segment remains in the system.

Those of skill know how to ascertain readily, for a particular probe and solid support, suitable stringency conditions and time periods for the hybridization and post-hybridization washes that will provide acceptable specificity and sensitivity for the assays in which the probe will be employed. See Meinkoth and Wahl, supra.

After unduplexed probe is washed from the system, a solution of reporter group, including a carbonic anhydrase conjugate to the tag moiety on the probe, is incubated with the solid support. Generally, a 10-fold to $10^6$-fold, usually $10^2$- to $10^4$-fold, molar excess of reporter group relative to tag moiety, will be present in the solution and the incubation will be carried out over a time sufficient to ensure that substantially all tag in the system is bound by reporter group. Then, unbound reporter group is washed from the system. Again, the skilled know how to determine conditions of incubation and post-incubation washing to ensure that most tag in a system is bound by reporter group and that little or no reporter group not associated with tag remains in a system.

The system is then treated appropriately to generate a signal from reporter group in the system. A determination is then made whether such a signal was generated.

If positive control was employed, signal from it is compared with that from blank to ensure that the assay system was functional. If the system was functional, the signal from positive control will be greater than that from blank.

The signal from test sample is compared with that from blank. If signal from test sample is greater than that from blank, target segment was present in the sample.

The invention is now illustrated in the following examples:

EXAMPLE I

Polynucleotides

The following polydeoxyribonucleotides were synthesized using automated solid-phase phosphoramidite methodology (Matteucci and Caruthers, J. Am. Chem. Soc. 103, 3185 (1981) and Beaucage and Caruthers, Tetrahedron Lett. 1981, 1859–1862) on a Model 380A Applied Biosystems DNA Synthesizer (Applied Biosystems, Inc., Foster City, Calif., U.S.A.). The oligonucleotides produced with the synthesizer have a free hydroxyl group at both the 5'-end and the 3'-end. From the mixture of polydeoxyribonucleotides of varying lengths produced in a synthesis on the machine, the desired one, which is the longest, is isolated and purified by high performance liquid choromatography (HPLC), utilizing a linear gradient of acetonitrile in 0.1M triethyl ammonium acetate (pH 7.0) to elute the polydeoxyribonucleotides, as described by Frank et al., Nucl. Acids Res. 11, 4365–4377 (1983) at pp. 4369–4370.

```
Polynucleotide A:  5'-GAAGGGGTATCTTTGGATAAAAG-3'
Polynucleotide B:  5'-CCACCACCTAGAACTAGGATATC-3'
Polynucleotide C:  5'-CCAGGCCAGCCGGAGGGACCCCGGGAGCCCGGGCG-3'
```

The sequence of Polynucleotide A is complementary to that of a segment of the alpha-mating factor gene of *Saccharomyces cerevisiae*. The sequence of Polynucleotide B is complementary to that of a segment of the alcohol oxidase gene of *Pichia pastoris*. The sequence of Polynucleotide C is complementary to that of a segment of the genome of Epstein-Barr virus.

EXAMPLE II

Preparation and Characterization of $N^4$-Amino-2'-Deoxycytidine

Deoxycytidine was converted to $N^4$-aminodeoxycytidine following the procedure of Negishi et al., (I) and (II) supra. To 1.0 g (4.4 mmoles) of deoxycytidine (Calbiochem-Behring, La Jolla, Calif. U.S.A.) was added 10 ml of 4M hydrazine, 0.1M bisulfite, 0.1M sodium phosphate buffer (to adjust pH to 7.0) and the solution was stirred at 60° C. for 4 hours. Then 90 ml of 95% ethanol was added, and the mixture was allowed to sit at −20° C. overnight. The buffer salts were removed by filtration and the filtrate was reduced to a thick oil under reduced pressure. Absolute ethanol was added to afford 270 mg (25%) of a semi-solid $N^4$-amino-2'-deoxycytidine.

To 10 mg (0.041 mmoles) of $N^4$-amino-deoxycytidine was added 10 mg (0.051 mmoles) of 2,4-dinitrobenzaldehyde in 5 ml of 50% aqueous methanol. After stirring for 15 minutes at 25° C., the orange precipitate which formed was filtered off. The hydrazone was purified by chromatography on silica gel using 10% methanol in chloroform as an eluent. After concentration of the peak fractions under reduced pressure, 12 mg (70%) of $N^4$-amino-deoxycytidine-2,4-dinitrophenylhydrazone was isolated and characterized by NMR spectroscopy. The product was further characterized by uv/vis spectroscopy yielding an extinction coefficient of 18,000 at 375 nm (dimethylsulfoxide (DMSO):water, 1:20).

EXAMPLE III

Polynucleotides with $N^4$-Aminocytosines

Cytosines in polynucleotides are modified by incubation at 37° C. in a mixture of 4M hydrazine with 1M sodium bisulfite buffered to pH 7 with 0.1M sodium phosphate, with polynucleotide dissolved to a concentration such that the concentration of cytosines is between about 1.0 and 100 micromolar. Under these conditions, the cytosines in a single-stranded polynucleotide are converted to $N^4$-aminoctyosines with pseudo first-order kinetics with a $t_{1/2}$ of about 30 minutes. Complete conversion occurs in about 4 hours.

In a typical reaction, 200 micrograms of polynucleotide A were incubated in 0.5 ml of 4M hydrazine, 1M sodium bisulfite, at pH 7.0 (sodium phosphate buffer) at 37° C. The kinetics of transamination were measured by two methods. In one, the reaction was stopped after various reaction times by separation of hydrazine and bisulfite from the polynucleotide by gel permeation chromatography and then the amount of $N^4$-aminocytosine was determined by reaction of 1 volume of a polynucleotide solution with 0.1 volumes of a solution of 2,4-dinitrobenzaldehyde (20 mg/ml) in dimethylformamide (DMF) for 30 minutes at 23° C., followed by a second gel permeation chromatography step. The amount of 2,4-dinitrophenylhydrazone-derivatized polynucleotide formed was measured spectrophotometrically. In the other method, the kinetics were determined by complete digestion of the polynucleotide with snake venom phosphodiesterase and subsequent analysis of the monomers by HPLC. Both methods of analysis yielded the same results. Modification of the polynucleotide was complete within 4 hours, and half complete at approximately 30 minutes.

EXAMPLE IV

Synthesis of Polynucleotides Using Bases with Modified Cytosines Directly

Polynucleotide probes can be synthesized by the solid-phase phosphoramidite method of Example I so as to have 4-aminocytosines at specific locations. In contrast, the procedure of Example III results in a random distribution of modified cytosines in the polynucleotide, governed by the mathematics of the Poisson distribution and nearest-neighbor effects. To synthesize a polynucleotide with $N^4$-aminocytosine in place of cytosine at specific locations, suitably protected $N^4$-aminocytidine or $N^4$-amino-2'-deoxycytidine is used in place of cytidine or 2'-deoxycytidine at the appropriate steps in the automated synthesis.

Cytidine or 2'-deoxycytidine is transformed into the corresponding $N^4$-amino analog by incubation in a solution of 4M hydrazine and 0.1M sodium bisulfite for 4 hours at 60° C., following the procedure of Example II (see also Negishi et al. (II), supra). The $N^4$-amino analog is isolated and purified as described by Negishi et al. (II), supra.

The $N^4$-amino-modified nucleosides are then protected for use in automated synthesis in the same manner as other nucleosides. In particular, the $N^4$-amino group, and the 3' and 5' hydroxyls, are perbenzoylated with benzoyl chloride. The 3′ and 5′ hydroxyls are then liberated by selective hydrolysis. The 5′-hydroxyl is then tritylated with 4′-dimethoxy tritylchloride, and the 3′-hydroxyl is phosphoramidited with methoxymonochloro-N,N-diisopropylaminophosphate. The resulting N-acyl, 5′-trityl, 3′-phosphoramidite derivative of cytidine or 2′-deoxycytidine is then used in the automated synthesizer in the appropriate steps to synthesize the nucleic acid of desired sequence. Removal of the benzoyl group from the N⁴-amino groups of the resulting modified polynucleotide proceeds along with deprotection of the other groups upon removal of the polynucleotides from the resin.

EXAMPLE V

PABSAT

In this Example, preparation of PABSAT is described. The preparation is illustrated in Scheme V.

To prepare a halophenyl or nitrophenyl analog of PABSAT, the corresponding halophenyl or nitrophenyl analog of p-acetamido-benzene sulfonylchloride (compound of Formula XIX) is used in the preparative procedure.

To a solution of 0.2 gm (1.1 mmoles) of aminothiadiazole (XX) in 4 ml of dry pyridine at 0° C. was added, dropwise, a solution of 0.28 gm (1.12 mmoles) of p-acetamido-benzenesulfonyl chloride in 3 ml of dry pyridine. The reaction mixture was subsequently warmed to 23° C., and magnetically stirred for 16 hours. After concentration under reduced pressure, the crude product was dissolved in methanol, and treated with activated charcoal, filtered, concentrated under reduced pressure, and purified by flash chromatography using methylene chloride-methanol (65:25) to give 0.31 gm of the benzolamide derivative (Compound XVIII) in 75% yield.

All references in the present specification to "flash chromatography" are to the method described by Still et al., J. Org. Chem. 43, 2923–2925 (1978).

To 0.14 gm (0.37 mmole) of Compound XVIII was added 3.5 ml of 1N HCl, and the reaction mixture was refluxed for three hours. On cooling, the solution was neutralized with ammonium hydroxide, and concentrated under reduced pressure to give a white solid in quantitative yield, which was pure PABSAT (compound of Formula XVII).

SCHEME V

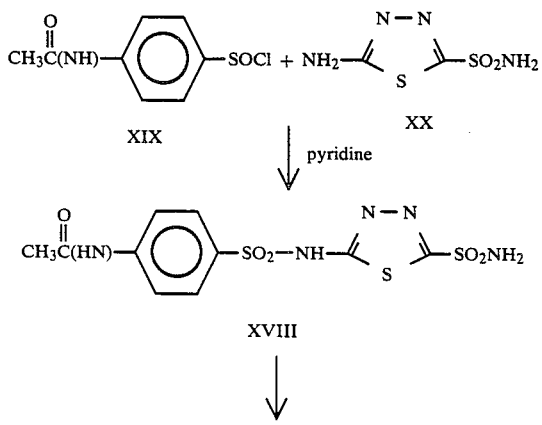

-continued
SCHEME V

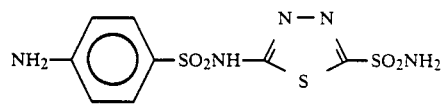

XVII

EXAMPLE VI

PABSAT-Linker Aldehyde

In this Example, methods are described for preparing linker-aldehyde compounds which are suitable for preparing probes of the invention by linking PABSAT (and halophenyl and nitrophenyl analogs thereof) to polynucleotides with N⁴-aminocytosine moieties, or with nucleoside bases otherwise modified with amino-terminated functional groups.

The methods of this Example are illustrated in Schemes VIA and VIB.

The methods can also be employed in preparing linker-aldehydes of aminothiaizole or sulfanilamide for linking those compounds to modified polynucleotides to make probes of the invention. This is accomplished by replacing PABSAT with aminothiadiazole or sulfanilamide in the reaction with the acetal acetyl chloride of Formula XXIII in Scheme VIB and preparing the aminothiadiazole or sulfanilamide linker-aldehyde from the resulting aminothiadiazole or sulfanilamide analog, respectively, of the acetal of Formula XXII.

SCHEME VIA

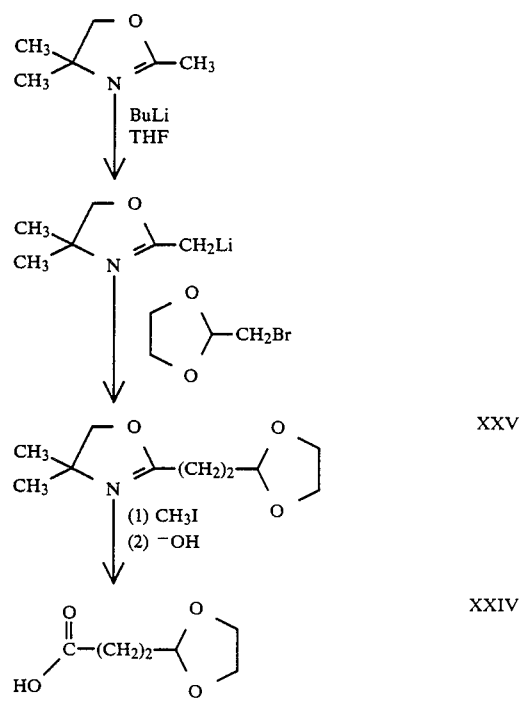

SCHEME VIB

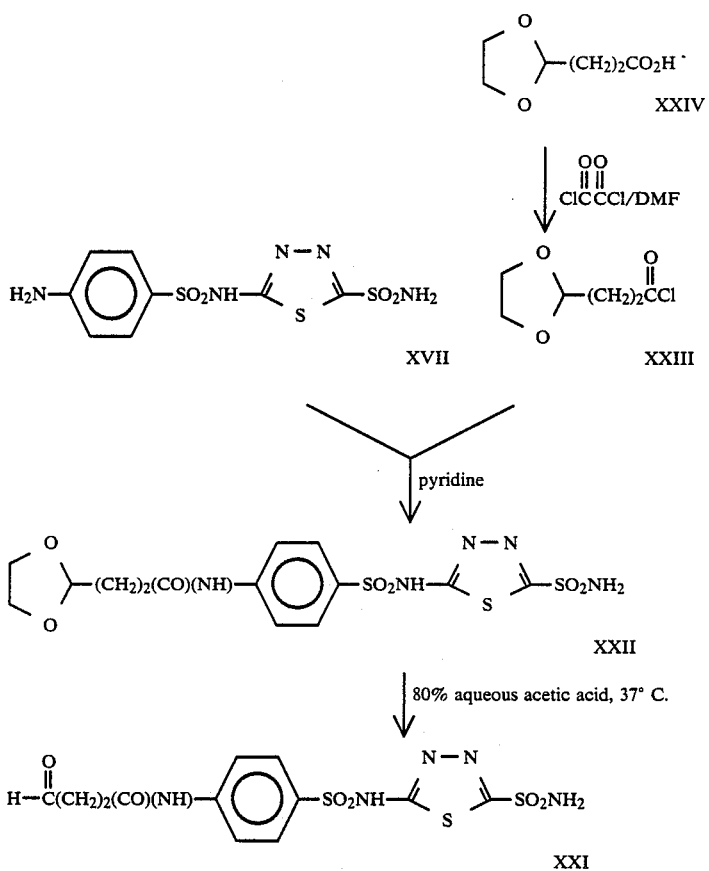

The compound of Formula XXV is prepared by the method of Meyers et al., J. Org. Chem. 39, 2778 (1974). 0.5 gm (4.4 mmole) of 2,4,4-trimethyloxazoline in 10 ml of dry THF is cooled to −78° C. and 3.1 ml of a 1.6M solution of butyl lithium in hexane (5 mmole butyl lithium) is added. A yellow precipitate results. To the solution (including precipitate) is added 0.52 ml (5 mmole) of 2-bromoethyl-1,3-dioxolane and the mixture is stirred for 30 minutes at −78° C. and then allowed to warm to 23° C., after which the mixture is poured into 30 ml of brine and the product is extracted with diethylether. The etheral solution is dried over $Na_2SO_4$ and concentrated under reduced pressure to afford the acetal oxazoline (Formula XXV).

To 0.6 gm (3 mmole) of the acetal-oxazoline of Formula XXV is added 2 ml of methyl iodide and the mixture is stirred for 16 hours at 23° C. After concentration under a stream of nitrogen, 5 ml of a 1N sodium hydroxide solution is added, and the mixture is stirred for 15 hours at 23° C. After neutralization with 10% hydrochloric acid, followed by extraction with ether, and concentration under vacuum, the desired acetal-acid of Formula XXIV is obtained.

To 0.29 gm (2 mmole) of the acetal-acid of Formula XXIV in 10 ml of dry benzene is added 0.7 ml (8 mmole) of oxalyl chloride and one drop of DMF. The solution is stirred for 10 minutes and concentrated under vacuum. The resulting oil (acylchloride of Formula XXIII) is then taken up in 10 ml pyridine, and 0.64 gm (2 mmole) of PABSAT (Formula XVII) is introduced as a solution in 10 ml of pyridine. The mixture is stirred for 5 hours, and then concentrated in vacuo. Flash chromatography of the crude using 30% methanol in chloroform affords the acetal-linker-benzolamide derivative of Formula XXII.

The compound of Formula XXII is converted to the desired PABSAT linker aldehyde of Formula XXI by treatment with 80% aqueous acetic acid for 3 hours at 37° C. followed by lyophilization.

EXAMPLE VII

PABSAT—Amino-terminated and Carboxylate-terminated Linkers

In this Example, methods are described for preparing amino-terminated and carboxylate-terminated linker compounds of PABSAT. These compounds are suitable for preparing probes of the invention by linking PABSAT (and halophenyl and nitrophenyl analogs thereof) to polynucleotides through terminal phosphates or at nucleoside bases which are modified with functional groups (terminated with a carboxylate or active ester group) that are reactive with an amino group or with functional groups (terminated with an amino group) that are reactive with a carboxylate group or an active ester group prepared from the carboxylate.

The methods of this Example can also be employed in preparing amino-terminated or carboxylate-terminated linker compounds of aminothiadiazole and sulfanilamide for linking those compounds to modified polynucleotides to make probes of the invention. This is accomplished by replacing PABSAT with aminothiadiazole or sulfanilamide as a starting material in the synthesis of the amino-terminated or carboxylate-terminated linker compound.

0.45 gm (1.4 mmole) of PABSAT is reacted at 23° C. for 24 hours in 50 ml of dimethylformamide with 0.32 gm (1.4 mmole) of tertbutyloxycarboxyl-6-aminohexanoic acid and 0.27 gm (1.4 mmole) of dicyclohexylcarbodiimide. The resulting compound, of

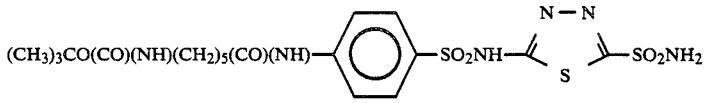

is isolated by chromatography on silica gel 60 employing 10% methanol in CHCl$_3$ as eluant. Removal of the BOC group (i.e., (CH$_3$)$_3$(CO)—) to obtain the amino-terminated linker compound of formula XXIX

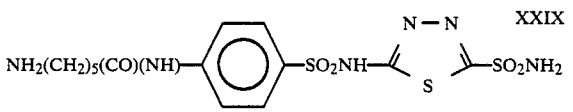

is effected by treatment with 25% trifluoroactetic acid in methylene chloride for 30 minutes at 23° C. followed by removal of solvent under reduced pressure.

The carboxylate-terminated PABSAT linker is prepared by reacting an approximately 10-fold molar excess (relative to PABSAT) of an anhydride of a dicarboxylic acid, such as glutaric or succinic anhydride, with PABSAT in dry pyridine (1 gm PABSAT per 50 ml pyridine) with a small amount of triethylamine (0.1 ml per gm PABSAT) and then isolating the linker compound by chromatography on silica gel 60 employing 40% methanol in methylene chloride as eluant.

EXAMPLE VIII

Probes With PABSAT, Aminothiadiazole or Sulfanilamide as Tag Moiety Linked to the N$^4$-Amino Group of N$^4$-Aminocytosines To prepare probe of the invention with PABSAT, aminothiadiazole or sulfanilamide as tag linked to N$^4$-amino group of N$^4$-aminocytosines, the following procedure is employed:

First, following the procedure of Example III, a polynucleotide with the sequence of the probe is modified to convert about 10 to about 50% of its cytosines into N$^4$-aminocytosines. The transamination reaction is stopped and modified polynucleotide is isolated by spin column chromatography employing a Sephadex G-25 spin column. The modified polynucleotide (approximately 75 ug in approximately 150 ul of effluent from the spin column chromatography procedure) is then mixed with 50 ul (5 mg/ml in DMSO) of a solution of sulfonamide linker aldehyde (e.g., compound of Formula XXI) prepared in accordance with Example VI. After 30 minutes at 37° C., labeled probe is obtained by spin column chromatography by passing the mixture (including unreacted aldehyde and labeled probe) through a Sephadex G-25 spin column and obtaining tagged polynucleotide (i.e., labeled probe) in the collected effluent.

Concentration of tagged probe is determined by UV absorbance at 260 nm. Attachment of tag is confirmed by detecting carbonic anhydrase polymer reporter group bound to tag, following procedures in Example X.

EXAMPLE IX

Probes with PABSAT, Aminothiadiazole or Sulfanilamide as Tag Moiety Linked to the 5-Position of Uracils This Example illustrates preparation of probe of the invention with PABSAT, aminothiadiazole or sulfanilamide as tag linked to the 5-position of uracils in place of the thymines at positions 9, 15, and 22 of Polynucleotide B (Example I).

Following the procedures of Ruth, published Patent Cooperation Treat Application No. WO 84/03285, a modified polynucleotide is synthesized with the sequence of polynucleotide B buth with uracil moieties of Formula

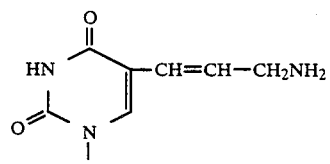

in place of the thymines at positions 9, 15, and 22.

The modified polynucleotide (approximately 75 microgram in 150 microliter of DMF) is mixed with a carbodiimide condensing agent, such as 1-ethyl-3,3-dimethylaminopropylcarbodiimide, and with 100 microliter of a solution (1 mg/ml with DMSO) of the carboxylate-terminated PABSAT linker compound prepared with glutaric anhydride as described in Example VII.

The reaction is continued at room temperature for 4 to 8 hours. Probe tagged with PABSAT is then obtained by passing the reaction mixture through a Sephadex G-25 spin column to separate the tagged probe from unreacted compound of Formula XXIX.

Concentration of tagged probe is determined by UV absorbance at 260 nm. Attachment of tag is confirmed by detecting carbonic anhydrase polymer reporter group bound to tag, following procedures in Example X.

EXAMPLE X

Use of Aminothiadiazole-Benzolamide Derivatized Probes in Hybridization Assays

In this Example, use of probes tagged with aminothiadiazole-benzolamide-derivative, carbonic anhydrase inhibitors, such as PABSAT, is described.

Following the procedure of Example IV, Polynucleotide C (Example I) is synthesized to have N$^4$-aminocytosines at positions 6, 20, 28, and 34.

Following the procedure of Example VIII, using PABSAT linker aldehyde of Formula XXII prepared as described in Example VI, the N$^4$-aminocytosine-containing Polynucleotide C is converted to probe with PABSAT linked to the $N^4$-amino nitrogens of the modified cytosines.

DNA is isolated from two mammalian cell cultures, one known to be infected with Epstein-Barr virus (EBV) and the other known to be EBV-free. Approximately 5 ug of protein-free DNA from each culture is affixed to a separate, prewetted nitrocellulose filter using standard slot-blotting techniques.

After drying in an oven under vacuum at 80° C., the filters are then pre-hybridized for 2 hours at 42° with 6× SSPE, 0.5% (w/v) sodium dodecyl sulfate (SDS), 1× Denhardt's Solution and 1 mg/ml herring sperm DNA.

Each filter is then hybridized with 1 ug of PABSAT-derivatized polynucleotide C, at 42° C. for 15 hours at 300 ng/ml in hybridization solution (6× SSPE, 0.5% (w/v) SDS, 1× Denhardt's Solution).

Following the hybridization, the filters are washed as follows:

2× SSC for 15 minutes, three times, at room temperature.

(Definitions of SSC, SSPE and Denhardt's Solution are known in the nucleic acid hybridization art. See Maniatis et al., Molecular Cloning: A Laboratory Manual, Cold Spring Harbor Laboratory Press, Cold Spring Harbor, N.Y., U.S.A. (1982).)

The filters are then cut to isolate the portions (blots) to which DNA had been affixed and these filter pieces are developed with a reporter system based on the fluorescein-diacetate assay of Leary et al. (1978), supra, for bovine erythrocyte carbonic anhydrase B as follows:

Bovine erythrocyte carbonic anhydrase B is purchased from Sigma Chemical Co., St. Louis, Mo., U.S.A. and purified as described by Armstrong et al., J. Biol. Chem. 244, 5137–5149 (1966). The purified protein is polymerized by the procedure of Epton, supra.

The filter pieces with hybridized probe are incubated for 5 minutes at room temperature with a solution of protein polymer (20 ug/ml) in Tris buffer (pH 7.6). After the incubation, the filter pieces are washed 5 times with 0.05M potassium phosphate buffer, pH 6.8, to remove protein polymer that has not bound to probe through PABSAT tag.

Finally, the filter pieces are incubated for 4 hours at room temperature with a solution of 1 mM fluorescein diacetate in 0.05M potassium phosphate buffer, pH 6.8.

After the incubation with fluorescein diacetate, the filter pieces to which EBV DNA had been affixed exhibit a fluorescent yellow-green color while the other filter pieces exhibit no fluorescence.

The same procedure is followed with probe of the invention prepared according to Example IX in an assay of a yeast culture for the presence of P. pastoris.

While the foregoing examples illustrate the present invention, they are not intended to limit the scope thereof. The skilled in the art will recognize, from the exemplified embodiments, modifications and variations that are within the spirit and scope of the invention described and claimed herein.

What is claimed is:

1. A single-stranded nucleic acid probe, of between about 12 to about 10,000 bases in length, which comprises:

(I) a terminal nucleotide bound, through (A) the 3'-carbon, if said terminal nucleotide is at the 3'-end of said probe, or (B) the 5'-carbon, if said terminal nucleotide is at the 5'-end of said probe, to a group of formula $-OPO_2(NH)(CH_2)_2R_6$; or (II) (i) a cytosine or uracil modified by covalent attachment to position 5 of a group $-R_1$, (ii) an adenine or guanine modified by covalent attachment to position 8 of a group $-R_1$, or (iii) a cystosine modified by covalent attachment to the $N^4$-nitrogen of a group of formula $-N=C(R_2)-R_8$, $-NH-CR_2H-R_8$ or $-NH(C=R_3)NH-R_8$, wherein $-R_1$ is $-CH_2CHR_5R_6$, $-CH_2R_5R_6$, $-CH=CR_5R_6$, $-CH=CR_5(CO)R_6$ or $-CH=CR_5(NHR_6)$, wherein $R_5$ is hydrogen or alkyl of 1 to 6 carbon atoms and $R_6$ is $-(CH_2)_mR_7$, wherein m is 0 to 12 and $R_7$ is $-(CO)(NH)R_8$ or $-(NH)(CO)R_8$, wherein $R_8$ is $-(CH_2)_pR_{32}$, wherein p is 2 to 20 and $R_{32}$ is:

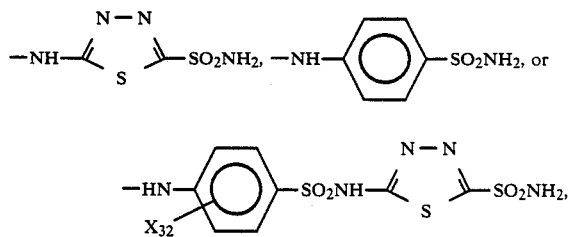

wherein $X_{32}$ is hydrogen, a halogen or $-NO_2$, wherein $R_2$ is hydrogen or alkyl of 1 to 4 carbon atoms, wherein $R_3$ is oxygen or sulfur, and wherein $R_{32}$ is bound with a reporter group which is an heteropolymer or homopolymer of a carbonic anhydrase, in which said carbonic anhydrase is the conjugate protein and is capable of catalyzing a reaction which yields a detectable signal.

2. A nucleic acid probe according to claim 1 which is between about 12 and about 100 nucleotides in length and which is labeled, only through the 5'-carbon of the 5'-terminal nucleotide and with a group, wherein, in $R_6$, m is 0 to 6 and p is 2 to 8, and wherein the carbonic anhydrase of the reporter group is a mammalian erythrocyte carbonic anhydrase B.

3. A nucleic acid probe according to claim 1 which is labeled only through between about 10% and about 60% of its nucleotide bases and wherein the carbonic anhydrase of the reporter group is a mammalian erythrocyte carbonic anhydrase B.

4. A nucleic acid probe according to claim 2 wherein $R_{32}$ is 2-(p-amino-benzenesulfonamido)-1,3,4-aminothiadiazole.

5. A nucleic acid probe according to claim 3 wherein $R_{32}$ is 2-(p-amino-benzenesulfonamido)-1,3,4-aminothiadiazole.

6. A process for making a single-stranded nucleic acid probe of known sequence which is between about 12 and about 10,000 bases in length which comprises binding a reporter group, which is a heteropolymer or homopolymer of a carbonic anhydrase, in which said carbonic anhydrase is the conjugate protein and is capable of catalyzing a reaction which yields a detectable signal, with a nucleic acid which has the same sequence as the probe and comprises a modified cytosine moiety of formula LVII:

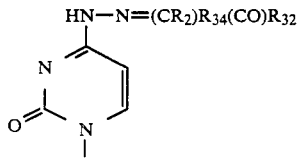

wherein $R_{32}$ is:

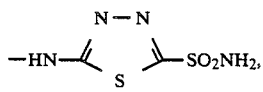

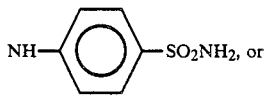

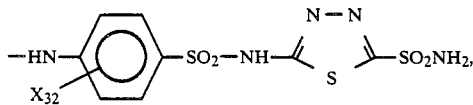

wherein $X_{32}$ is hydrogen, a halogen or —$NO_2$; wherein $R_2$ is hydrogen; and wherein $R_{34}$ is alkyl of 2 to 20 carbon atoms.

7. A process according to claim 6 wherein the nucleic acid has between about 10% and about 60% of its cytosines modified to $N^4$-aminocytosines.

8. A process according to claim 7 wherein $R_{34}$ is n-alkyl of 2 to 8 carbon atoms and $R_{32}$ is 2-(p-aminobenzenesulfonamido)-1,3,4-aminothiadiazole.

9. A process for making a single-stranded nucleic acid probe of known sequence which is between about 12 to about 10,000 bases in length, which comprises binding a reporter group, which is a heteropolymer or homopolymer of a carbonic anhydrase, in which said carbonic anhydrase is the conjugate protein and is capable of catalyzing a reaction which yields a detectable signal, with a nucleic acid which has the same sequence as the probe and comprises (i) a cytosine or uracil modified by covalent attachment to position 5 of a group —$R_1$ or (ii) an adenine or guanine modified by covalent attachment to position 8 of a group —$R_1$, wherein —$R_1$ is —$CH_2CHR_5R_6$, —$CH=CR_5R_6$, —$CHR_5R_6$, —$CH=CR_5(CO)R_6$ or —$CH=CR_5(NHR_6)$, wherein $R_5$ is hydrogen or alkyl of 1 to 6 carbon atoms and $R_6$ is —$(CH_2)_mR_7$, wherein m is 0 to 12 and $R_7$ is —(-CO)(NH)$R_8$ or —(NH)(CO)$R_8$, wherein $R_8$ is —$(CH_2)_pR_{32}$, wherein p is 2 to 20 and $R_{32}$ is:

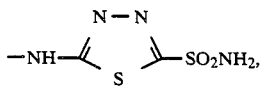

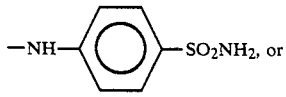

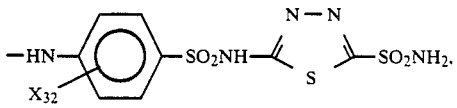

wherein $X_{32}$ is hydrogen, a halogen or —$NO_2$.

10. A process according to claim 9 wherein the nucleic acid is between about 12 and about 100 bases in length.

11. A process according to claim 10 wherein $R_1$ is —$CH=CR_5R_6$, wherein $R_5$ is hydrogen; wherein $R_6$ is —$(CH_2)_mR_7$; wherein m is 1 to 4; wherein $R_7$ is —(NH)-(CO)$R_8$, wherein $R_8$ is —$(CH_2)_pR_{32}$; wherein p is 2 to 8; and wherein $R_{32}$ is 2-(p-amino-benzenesulfonamido)-1,3,4-aminothiadiazole.

12. A method for testing a sample for the presence of a biological entity, associated with a target DNA or RNA, which comprises:

(i) combining single-stranded nucleic acid of the sample with a modified nucleic acid for the target DNA or RNA, said modified nucleic acid being single-stranded, being between about 12 to about 10,000 bases in length, comprising (a) a nucleotide modified to include a group which comprises a tag moiety that is an aromatic sulfonamide inhibitor of a carbonic anhydrase or (b) a terminal nucleotide bound through a terminal phosphate to a group which comprises a tag moiety that is an aromatic sulfonamide inhibitor of a carbonic anhydrase, provided that the sequence of said modified nucleic acid is such that, and the derivation of single-stranded nucleic acid from said sample and the combining of said single-stranded nucleic acid with said modified nucleic acid are carried out under conditions such that, stable duplexes form between said modified nucleic acid and at least a portion of the target DNA or RNA present in said sample but not significantly between modified nucleic acid and non-target DNA or RNA; and (ii) determining whether stable duplex was formed in step (i) by (a) separating unduplexed modified nucleic acid from duplexed probe formed in step (i);

(b) binding the duplexed modified nucleic acid with a reporter group, which is a homopolymer or heteropolymer of a carbonic anhydrase, in which said carbonic anhydrase is the conjugate protein and is capable of catalyzing a reaction which yields a detectable signal, said binding being under conditions whereby the reporter group binds to at least a portion of any of said tag moiety that is present, and separating from the duplexed modified nucleic acid so treated substantially all unbound reporter group;

(c) treating the product of step (i), after treatment according to step (ii)(a) and step (ii)(b), to produce a signal from any of said reporter group that is present; and (d) determining whether a detectable signal is generated by the treatment of step (ii)(c) as an indicator of the presence of the biological entity in the sample.

13. A method according to claim 12 wherein the tag moiety is an aromatic sulfonamide inhibitor of a mammalian erythrocyte carbonic anhydrase B and the reporter group is a homopolymer or heteropolymer of a mammalian erythrocyte carbonic anhydrase B inhibited by the tag moiety.

14. A method according to claim 13 wherein the tag moiety is a moiety selected from the group consisting of:

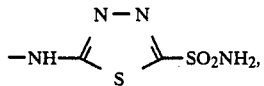

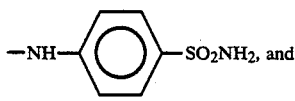

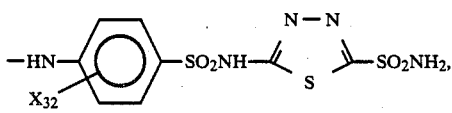

wherein $X_{32}$ is hydrogen, a halogen or $-NO_2$.

15. A method according to claim 14 wherein the modified nucleic acid comprises (i) a cytosine or uracil modified by covalent attachment to position 5 of a group $-R_1$, (ii) an adenine or guanine modified by covalent attachment to position 8 of a group $-R_1$, or (iii) a cytosine modified by covalent attachment to the $N^4$-nitrogen of a group $-N=C(R_2)-R_8$, $-NH-CR_2H-R_8$ or $-NH(C=R_3)NH-R_8$, wherein $-R_1$ is $-CH=CR_5R_6$, $-CH_2R_5R_6$, $-CH_2CHR_5R_6$, $-CH=CR_5(CO)R_6$ or $-CH=CR_5(NHR_6)$, wherein $R_5$ is hydrogen or alkyl of 1 to 6 carbon atoms and $R_6$ is $-(CH_2)_mR_7$, wherein m is 0 to 12 and $R_7$ is $-(CO)(NH)R_8$ or $-(NH)(CO)R_8$, wherein $R_8$ is $-(CH_2)_pR_{32}$, wherein p is 2 to 20 and $R_{32}$ is

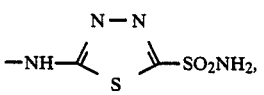

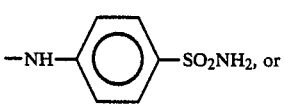

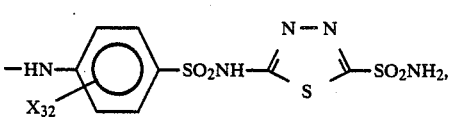

wherein $X_{32}$ is hydrogen, a halogen or $-NO_2$; wherein $R_2$ is hydrogen or alkyl of 1 to 4 carbon atoms; and wherein $R_3$ is oxygen or sulfur.

16. A method according to claim 15 wherein the modified nucleic acid comprises a cytosine modified by covalent attachment to the $N^4$-nitrogen of a group $-N=C(R_2)-R_8$, $-NH-CR_2H-R_8$ or $-NH(C=R_3)NH-R_8$, wherein $R_2$ is hydrogen or alkyl of 1 to 4 carbon atoms, $R_3$ is oxygen or sulfur and $R_8$ is $-(CH_2)_pR_{32}$, wherein p is 2 to 20 and $R_{32}$ is

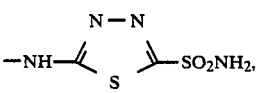

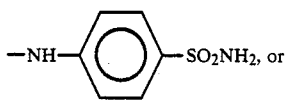

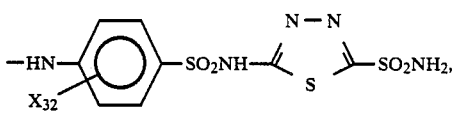

wherein $X_{32}$ is hydrogen, a halogen or $-NO_2$.

17. A method according to claim 16 wherein, in the probe, the group covalently attached to the $N^4$-nitrogen has the formula $-N=CH(CH_2)_pR_{32}$, wherein
p is 2 to 8 and $R_{32}$ is
2-(p-amino-benzenesulfonamido)-1,3,4-aminothiadiazole.

18. An enzyme immunoassay, for detecting antibody comprising an (i) combining sample suspected of containing antibody with an enzyme-labeled specific binder for said antibody; (ii) separating bound from unbound enzyme-labeled specific binder; and (iii) determining activity of enzyme-label as an indicator of the presence of antibody in the sample, wherein the improvement comprises employing as the enzyme-labeled specific binder for detecting antibody an inhibitor-derivatized anti-IgG, anti-IgM or S. aureus Protein A that is labeled with a heteropolymer or homopolymer of a carbonic anhydrase that is inhibited by the inhibitor, wherein said inhibitor comprises group of formula I:

wherein $R_{32}$ is:

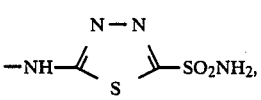

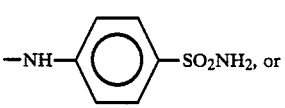

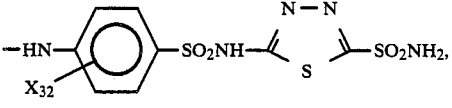

wherein $R_{34}$ is an alkyl of 2 to 20 carbon atoms, wherein $R_{91}$ is bonded to an amine group of said anti-IgG, anti-IgM or Protein A and is $-(CO)-$, $-(NH)(C=O)-$ or $-(NH)(C=S)-$ and $R_{32}$ is bound with a reporter group, which is said heteropolymer or homopolymer of a carbonic anhydrase, in which said carbonic anhydrase is the conjugate protein and is capable of catalyzing a reaction which yields a detectable signal.

19. An enzyme immunoassay according to claim 18 wherein $R_{34}$ is n-alkyl of 2 to 8 carbon atoms, wherein $R_{91}$ is $-CO-$, and wherein the reporter group is a homopolymer of a mammalian erythrocyte carbonic anhydrase B.

20. An enzyme immunoassay according to claim 19 which is an enzyme-linked immunosorbent assay.

* * * * *